(12) United States Patent
Wilson et al.

(10) Patent No.: US 6,974,678 B2
(45) Date of Patent: Dec. 13, 2005

(54) MICRO-FLUIDIC DEVICE FOR MEASURING OSMOTIC SECOND VIRIAL COEFFICIENTS

(75) Inventors: Wilbur W. Wilson, Starkville, MS (US); Charles S. Henry, Fort Collins, CO (US); Carlos D. Garcia, Cordoba (AR)

(73) Assignee: Mississippi State University, Mississippi State, MS (US)

( * ) Notice: Subject to any disclaimer, the term of this patent is extended or adjusted under 35 U.S.C. 154(b) by 328 days.

(21) Appl. No.: 10/265,715

(22) Filed: Oct. 8, 2002

(65) Prior Publication Data

US 2004/0067577 A1 Apr. 8, 2004

(51) Int. Cl.[7] .................................................. C12Q 1/37
(52) U.S. Cl. .......................................... 435/23; 435/7.1
(58) Field of Search ........................... 435/23, 7.1, 177, 435/180, 288.5, 817; 422/58, 68.1; 216/2

(56) References Cited

U.S. PATENT DOCUMENTS

| | | | | |
|---|---|---|---|---|
| 6,123,819 A | * | 9/2000 | Peeters | 204/452 |
| 6,361,958 B1 | * | 3/2002 | Shieh et al. | 435/7.1 |
| 6,524,790 B1 | * | 2/2003 | Kopf-Sill et al. | 435/6 |
| 6,585,939 B1 | | 7/2003 | Dapprich | |
| 6,599,436 B1 | | 7/2003 | Matzke et al. | |
| 6,613,512 B1 | | 9/2003 | Kopf-Sill et al. | |
| 6,649,358 B1 | * | 11/2003 | Parce et al. | 435/7.2 |
| 6,699,665 B1 | * | 3/2004 | Kim et al. | 435/6 |
| 2002/0076350 A1 | | 6/2002 | Weigl, et al. | |
| 2003/0087290 A1 | * | 5/2003 | Tarlov et al. | 435/6 |

OTHER PUBLICATIONS

Buranda T. Biomolecular Recognition on Well Characterized Beads Packed in Microfluidic Channels. Analytical Chemistry 74(5)1149–1156, 2002.*
Hage D. Affinity Chromatography. Handbook of HPLC Marcel Dekker, 483–498, 1998.*
Pawlak M. Zeptosens' Protein Microarrays. Proteomics 2(4)383–393, 2002.*
Tessier P. Rapid Measurement of Protein Osmotic Second Virial Coefficients by Self Interation Chromatography. Biophysical J vol. 82, 1620–1631, Mar. 2002.*
Hage, D. High Performance Affinity Chromatography. J of Chromatography B 768:3–30, 2002.*
Wang, "Electrochemical Detection for Microscale Analytical Systems: A Review", Talanta, 56, 223–231 (2002).
Khandurina, et al., "Bioanalysis in Microfluidic Devices", Journal of Chromatography A, 943, 159–183 (2002).
McEnery, et al., "Liquid Chromatography On–Chip: Progression Towards a $\mu$–Total Analysis System", The Analyst Communication, 125, 25–27 (2000).
Duffy, et al., "Rapid Prototyping Microfluidic Systems in Poly(dimethylsiloxane)", Anal. Chem., 70, 23, 4974–4984 (1998).
Björkman, et al., "Diamond Microchips for Fast Chromatography of Proteins", Sensors and Actuators B, 79, 71–77 (2001).
Becker, et al., "Polymer Microfluidic Devices", Talanta, 56, 267–287 (2002).
Duffy, et al., "Rapid Prototyping of Microfluidic Switches in Poly(dimethyl siloxane) and Their Actuation by Electro–Osmotic Flow", J. Micromech. Microeng., 9, 211–217 (1999).
Quin, et al., "Microfabrication, Microstructures and Microsystems", Microsystem Technology in Chemistry and Life Sciences, Chapter 1, Springer–Verlag Berlin, Heidelberg, Germany (1998).
Hage, "Affinity Chromatography", Handbook of HPLC, Cazez, T. (ed), Marcel Dekker, 483–498 (1998).
Tessier, et al., "Rapid Measurement of Protein Osmotic Second Viral Coefficients by Self–Interaction Chromatography", Biophysical Journal, 82, 1620–1631 (2002).
George, et al., "Predicting Protein Crystallization from a Dilute Solution Property", Acta Cryst., D50, 361–365 (1994).
Guo, et al., "Correlation of Second Virial Coefficients and Solubilities Useful in Protein Crystal Growth", J. Crystal Growth, 196, 424–433 (1999).
Hage, "High–Performance Affinity Chromatography: A Powerful Tool for Studying Serum Protein Binding", Journal of Chromatography B, 768, 3–30 (2002).
Aubry, "Applications of Affinity Chromatography to the Study of Drug–Melanin Binding Interactions", Journal of Chromatography B, 768, 67–74 (2002).
Patro, et al., "Self–Interaction Chromatography: A Tool for the Study of Protein–Protein Interactions in Bioprocessing Environments", Biotechnology and Bioengineering, 52, 193–203 (1996).
Chayen, et al., "Is Lysozyme Really the Ideal Model Protein?", Journal of Crystal Growth, 232, 262–264 (2001).
Pechkova, et al., "Accelerated Protein Crystal Growth by Protein Thin Film Template", Journal of Crystal Growth, 231, 599–602 (2001).
Stenstam, et al., "The Lysozyme–Dodecyl Sulfate System: An Example of Protein–Surfactant Aggregation", Langmuir, 17, 7513–7520 (2001).

(Continued)

Primary Examiner—Ralph Gitomer
(74) Attorney, Agent, or Firm—Piper Rudnick LLP; Steven B. Kelber

(57) ABSTRACT

A micro-fluidic device having a cavity containing a solid support (e.g., a plurality of particles) and a biomolecule immobilized on a surface of the solid support is provided. The micro-fluidic device can be used to monitor interactions between a biomolecule in a sample and the biomolecule immobilized on the solid support. For example, the micro-fluidic device can be used to monitor protein self-interactions wherein the protein in the sample is the same protein as that immobilized on the surface of the solid support. A method of making the micro-fluidic device is also described. The micro-fluidic device can be used for chromatographic applications where sample consumption is crucial.

11 Claims, 7 Drawing Sheets

OTHER PUBLICATIONS

Nakamura, et al., "Effect of Type and Concentration of Coupling Buffer on Coupling Yield in the Coupling of Proteins to a Tresyl–Activated Supported for Affinity Chromatography", 513, 367–369 (1990).

Tan, et al., "Miniaturized capillary isoelectric focusing in plastic microfluidic devices", Electrophoresis, vol. 23, No. 20, pp. 3638–3645, 2002.

Liu, et al., "Conductivity Detection for Monitoring Mixing Reactions in Microfluidic Devices", Analyst., vol. 126, No. 8, pp. 1248–1251, 2001.

Yang, et al., "Generation of Concentration Gradient by Controlled Flow Distribution and Diffusive Mixing in a Microfluidic Chip", Lab on a Chip, vol. 2, No. 3, 158–163, 2002.

* cited by examiner

MICRO-FLUIDIC DEVICE FOR MEASURING OSMOTIC SECOND VIRIAL COEFFICIENTS

STATEMENT REGARDING FEDERALLY SPONSORED RESEARCH OR DEVELOPMENT

This invention was made with Government support under NAG8-1837 awarded by the National Aeronautics and Space Administration. The Government has certain rights in the invention.

BACKGROUND OF THE INVENTION

1. Field of the Invention

The present invention relates generally to devices for monitoring interactions between biomolecules such as protein-ligand and protein-protein interactions. In particular, the present invention relates to a micro-fluidic device and to methods of using the micro-fluidic device to monitor biomolecular interactions.

2. Background of the Technology

In the last decade microfabrication technologies, originally developed for the silicon-based microelectronics industry, have spread out in a variety of applications as chemical and biochemical analysis tools (Wang, "Electrochemical Detection for Microscale Analytical Systems: A Review", Talanta, 56, 2, 11, 223–231 (2002)). The progress in this area has been focused on the rapidly developing fields of genomics, proteomics and metabolomics. It has also become evident that there is a tremendous market potential for microdevices aiding in diagnostics, drug discovery and evaluation of new pharmaceuticals, since these devices are expected to satisfy the urgent demand of high-throughput and large scale applications (Khandurina et al., "Bioanalysis in Microfluidic Devices", Journal of Chromatog., A 943, 159–183 (2002)). Some advantages of miniaturizing chemical and bioanalytical tools include performance, speed, throughput, reduced cost, low sample and reagent consumption and the possibility of parallel and integrated analysis (McEnery et al., "Liquid Chromatography On-Chip: Progression Towards a $\mu$-Total Analysis System", Analyst, 125, 25–27 (2002)).

Micro-fluidic devices have typically been fabricated in glass or oxidized silicon ($Si/SiO_2$). This approach to fabrication is successful, but is also slow and involves expensive instrumentation and complicated processes. See, for example, Duffy et al., "Rapid Prototyping Microfluidic System in Poly(dimethylsiloxane)", Anal. Chem., 70, 4974–4984 (1998) and Björkman, et al., "Diamond Microchips for Fast Chromatography of Proteins: Sensors and Actuators", B 79, 71–77 (2001)). As an alternative, polymers have been recognized as attractive materials for fabricating micro-fluidic devices. See, for example, Becker, et al., "Polymer Microfluidic Devices", Talanta, 56, 267–287 (2002); Duffy et al., "Rapid Prototyping of Microfluidic Switches in Poly(dimethylsiloxane) and Their Actuation by Electro-osmotic Flow", J. Micromech. Microeng., 9, 211–217 (1999); and Quin, et al., "Microfabrication, Microstructures and Microsystems", Microsystem Technology in Chemistry and Life Sciences, Chapter 1, Springer-Verlag Berlin, Heidelberg Germany (1998).

There still exists a need, however, for inexpensive and rapid manufacturing techniques for micro-fluidic devices, particularly for devices which allow the interactions between biomolecules such as proteins to be studied.

SUMMARY OF THE INVENTION

According to a first aspect of the invention, a micro-fluidic device is provided. According to this aspect of the invention, the micro-fluidic device comprises: a channel layer having a channel formed therein; a cover layer disposed on the channel layer over the channel, wherein the channel and cover layer form a cavity; a first opening in the channel layer and/or cover layer in fluid communication with the cavity; a second opening in the channel layer and/or cover layer in fluid communication with the cavity; a solid support located inside the cavity; and a biomolecule immobilized on a surface of the solid support.

According to a second aspect of the invention, a method of measuring interactions between a first biomolecule and a second biomolecule is provided. The method according to this aspect of the invention comprises: flowing a solution through a micro-fluidic device comprising a solid support contained in a cavity, wherein the first biomolecule is immobilized on a surface of the solid support; injecting a sample comprising the second biomolecule into the flowing solution upstream of the cavity; and measuring the time required for the second biomolecule to emerge from the cavity ($t_R$). According to this aspect of the invention, the cavity has an internal volume of 100 $\mu$l or less and the time required for the second biomolecule to emerge from the cavity ($t_R$) is a measure of the presence and/or degree of interaction between the first biomolecule and the second biomolecule.

According to a third aspect of the invention, a method of making a micro-fluidic device is provided. According to this aspect of the invention, the method comprises: casting a composition onto a positive relief surface, the positive relief surface comprising a raised region; allowing the composition to solidify; removing the solidified composition from the positive relief surface to form a channel layer, the channel layer having a channel corresponding to the raised elongate region; disposing a cover layer on the channel layer over the channel to form a cavity; forming an inlet in fluid communication with the cavity; forming an outlet in fluid communication with the cavity; and packing the cavity with a solid support, wherein a biomolecule is immobilized on a surface of the solid support.

BRIEF DESCRIPTION OF THE DRAWINGS

The present invention may be better understood with reference to the accompanying drawings in which.

DETAILED DESCRIPTION OF THE PREFERRED EMBODIMENTS

Figure 1A:
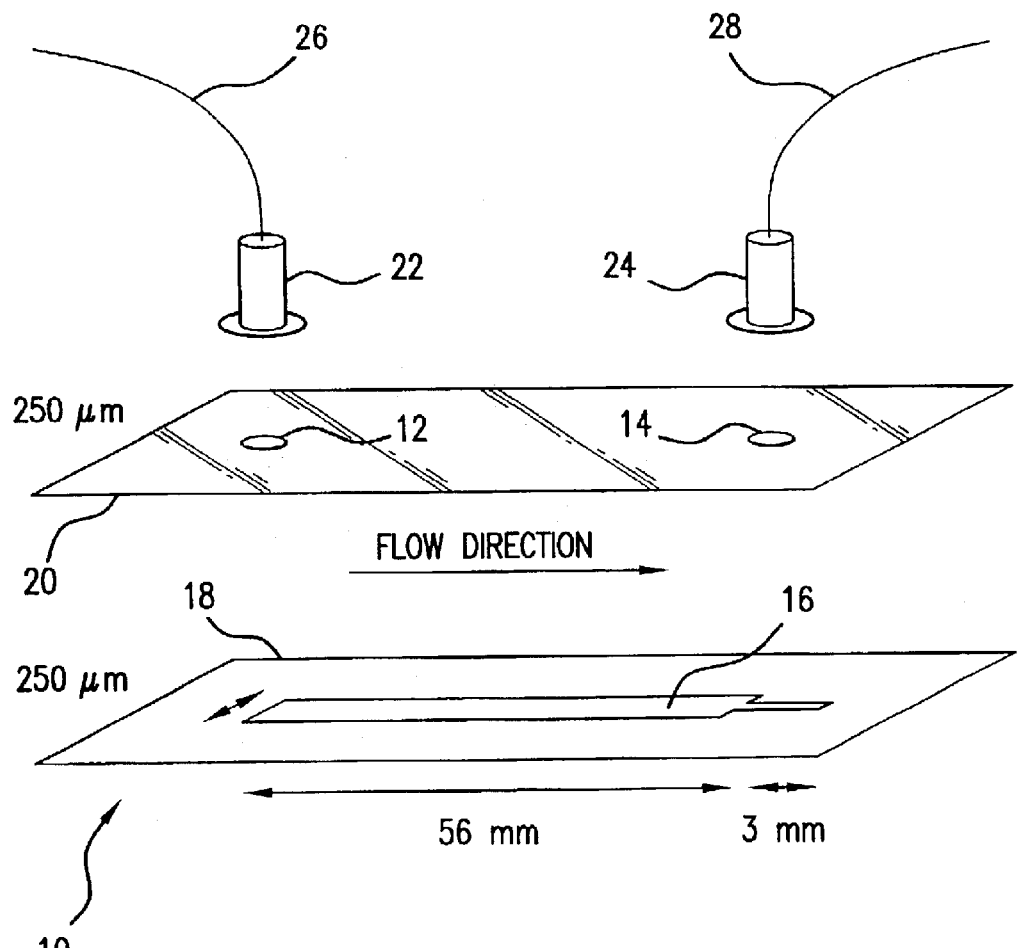
FIG. 1A is a schematic showing a micro-fluidic device according to the invention.

The device according to the present invention is capable of studying interactions between biomolecules (e.g., proteins). According to the invention, three different types of biomolecular interactions can be studied. First, the biomolecules can be the same. This technique is referred to as self-interaction chromatography (SIC) and can, for example, be used to rapidly screen for solution conditions favorable for protein crystallization.

Second, when one of the biomolecules is a small molecule (i.e., a ligand), the method according to the invention can be used to screen for interactions between the ligand and a protein. When the ligand is a drug, this technique can be useful in the development of new drugs. According to the invention, different drugs can be screened for their interaction with a given protein of interest (e.g., the interaction between digitoxin and human serum albumin can be studied).

Third, the biomolecule in the sample can be a different biomolecule than that bound to the stationary phase. In this case, the measurement of the biomolecular interaction can allow the function of the biomolecule (e.g., protein) to be determined.

In addition, using a micro-fluidic device according to the invention, the ability of a compound (i.e., a drug) to disrupt the interaction of two proteins can be studied.

All of the above applications are related to affinity chromatography. Conventional affinity chromatography, however, requires relatively large amounts of protein and ligand. According to the present invention, measurements of protein-ligand interactions can be made very rapidly with minimal protein and ligand consumed.

Devices according to the invention can also be used in so called "low performance" affinity chromatography applications wherein large diameter gel particles are typically used as the support material. These devices can be operated with a peristaltic pump or even under gravity flow due to the low back pressure. See, for example, Hage, "Affinity Chromatography", Handboook of HPLC, Cazez, T. Ed.; Marcel Dekker, 483–498 (1998).

Self-Interaction Chromatography can also be used to evaluate suitable solution conditions for protein crystal growth. The osmotic second virial coefficient ($B_{22}$) has been shown to correlate with crystallization behavior of proteins. See, for example, Tessier, et al., "Rapid Measurement of Protein Osmotic Second Virial Coefficients by Self-Interaction Chromatography", Biophys. J., 82, 1620–1631 (2002) and George, et al., "Predicting Protein Crystallization from a Dilute Solution Property", Acta Crystalogr., D 50, 361 (1994). The determination of $B_{22}$ by static light scattering is well accepted as a reference method to evaluate protein-protein interactions, but is generally labor intensive, time consuming, and requires large amounts of protein (Tessier, et al., "Rapid Measurement of Protein Osmotic Second Virial Coefficients by Self-Interaction Chromatography", Biophys. J., 82, 1620–1631 (2002)).

For SIC applications, the second virial coefficient ($B_{22}$) has been correlated with the chromatographic capacity factor (k') which is represented by the following equation:

$$k' = \frac{t_R - t_m}{t_m} \quad \text{(Eq. 1)}$$

wherein $t_R$ is the retention time of the protein of interest and $t_m$ is the retention time of a non-interacting marker. Under conditions where the proteins experience net attraction, a slightly negative value of $B_{22}$ is obtained by static light scattering (SLS) (Guo, et al., "Correlation of Second Virial Coefficients and Solubilities Useful in Protein Crystal Growth", J. Cryst. Growth, 196, 424–433 (1999)). Under similar conditions, a positive k' value is obtained using SIC due to the larger retention time ($t_R$) of the protein in the sample with respect to the non-interacting marker ($t_m$). The opposite is also true. That is, if the proteins repel each other under the test conditions, a positive $B_{22}$ value is obtained by SLS whereas a negative k' value is obtained by SIC since, under these conditions, the protein in the sample will have a smaller retention time ($t_R$) than the non-interacting marker ($t_m$).

All of the data presented below are for self-interaction chromatography (SIC). SIC is a special case of affinity chromatography wherein the target molecule is used as both ligand (attached to the stationary phase) and ligate (soluble in the mobile phase). See, for example, Hage, "High-performance affinity chromatography: a powerful tool for studying serum protein binding", Journal of Chromatog. B. 768 (2002) 3–30 and Aubry, "Applications of Affinity Chromatography to the study of drug-melanin binding interactions", Journal of Chromatog. B. 768 (2002) 67–74.

In addition to measuring biomolecular interactions, this technique can also allow for the screening of protein formulation additives as physical stabilizers against aggregation as shown in Patro, et al., "Self-Interaction Chromatography: A Tools for the Study of Protein-Protein Interactions in Bioprocessing Environments", Biotechnol. Bioeng., 52,193–203 (1996)).

Due to extensive data in the literature, lysozyme is used herein as a model protein since it serves as a good example for nucleation and crystallization mechanisms studies under various conditions (Cheyen et al., "Is Lysozyme Really the Ideal Model Protein?", J. Cryst. Growth, 232, 262–264 (2001) and Pechkova, et al., "Accelerated Protein Crystal Growth by Protein Thin Film Template", J. Cryst. Growth, 231, 599–602 (2001). Lysozyme is a small (14.4 kDa) globular enzyme that is structurally stable over a wide range of pH values, temperatures and salt solutions (Stenstam, et al., "The Lysozyme-Dodecyl Sulfate System: An Example of Protein-Surfactant Aggregation", Langmuir, 17, 7513–7520 (2001)).

According to the present invention, an SIC system was fabricated on a micro-fluidic scale thus allowing the rapid and accurate analysis of protein-protein interactions using a small amount of sample. Simple procedures for the preparation of a micro-fluidic made from PDMS and a stationary phase for use with the micro-fluidic device are described below. Results for k' obtained using a micro-fluidic device according to the invention are compared with previously published data for $B_{22}$ obtained by static light scattering and showed very good correlation. Further, by using a micro-fluidic device according to the invention, a very small amount of sample protein (e.g., less than 37 ng) per injection was needed. The effects of flow rate, sample concentration and bound protein on the k' value are also shown below.

Experimental 2-1-Reagents and Solutions

For the preparation of the mold, SU-8 50 photoresist and XP SU-8 developer were used (Microchem Corp). Sylgard 184 silicone elastomer and curing agent were obtained from Dow Corning. Aqueous solutions were prepared using analytical grade reagents and 18 MΩ resistance water (Nanopure, Barnstead). Mobile phase solutions were prepared by dissolving 60.1 g of glacial acetic acid (Fisher) in 400 mL of water, adjusting the pH to 4.20 using a NaOH (Fisher) saturated solution and then diluting to 500 mL with water. Working solutions were prepared by diluting the former in a 1/20 ratio and adding the corresponding amount of NaCl. Phosphate buffer was prepared by dissolving 3.6 g of $Na_2HPO_4 \cdot 12H_2O$ (Acros Organics) in 70 mL of water, adjusting the pH to 8.00 with HCl and adjusting the final volume to 100 mL with deionized water. Lysozyme (LYS) (Roche) sample solutions were prepared one hour before each experiment by dissolving the desired amount of the dry protein in 1 mL of the corresponding solution. For the pH measurements, a combined glass electrode (Accumel) and a digital pH meter (Denver Instrument) were used. Methanol, hydrogen peroxide and sulfuric acid were ACS certified quality and provided by Fisher. Toyopearl AF-Tresyl-650M chromatography particles (TosoHaas) were used, after the below described modification step, as stationary phase. All experiments were performed at room temperature (22±2° C.).

2-2-LC-System

The LC system consisted of a syringe pump (PHD 4400 Harvard Apparatus) with a disposable 2.5 ml syringe, a sample injector (7520, Rheodyne) with a 0.2 µl loop, a UV-Vis detector (CE-1575, Jasco) at 280 nm, a data acquisition system and the interconnecting PEEK tubing (100 µm I.D.).

Fabrication of PDMS Device

A 3-inch silicon wafer (Silicon Valley Microelectronics Inc.) was cleaned and oxidized with piranha solution (2:1 $H_2SO_4:H_2O_2$). The wafer was then coated with SU-8 50 negative photoresist using a spin coater (Laurel Technologies) by dispensing approximately 3 mL of the photoresist. A spread cycle at 500 rpm for 12 seconds followed by a spin cycle at 1000 rpm during 30 seconds were performed followed by two baking steps at 65° C. and 95° C. for 5 and 30 minutes, respectively, to evaporate the solvent and densify the film. A digitally produced mask containing the channel pattern (56 mm long, 250 µm wide+3 mm long, 50 µm wide) was placed on the coated wafer, exposed to light via a near-UV flood source for 900 seconds and then baked at 95° C. for 13 minutes. The positive relief was then developed by removing the unexposed photoresist by placing the wafer in propylene glycol methyl ether acetate for 15 minutes, flushed with $H_2O$, methanol and dried under a $N_2$ stream. The height of the positive patterns, which are equal to the channels depth created on the PDMS layer, were measured with a profilometer and were 127 µm±7 µm (n=3). The dimensions of the channel are summarized in FIG. 1A. The PDMS layer was fabricated by pouring a degassed mixture of Sylgard 184 silicone elastomer and curing agent (10:1) onto the master and, after curing it for at least 3 hours at 65° C., peeling it from the mold.

As shown in FIG. 1A, the micro-fluidic device can consist of two different width channels. As shown, the broader channel (56 mm long, 250 µm wide) was used to place the solid support (e.g., particles) and the thinner channel (3 mm long, 50 µm wide) was used as a frit.

Chip Assembly

A schematic drawing of a micro-fluidic device 10 according to the invention is shown in FIG. 1A. As shown in FIG. 1A, two openings 12, 14 (1 mm diameter) are formed through a microscope glass slide 20 (25×75×1 mm, Fisherbrand) which is used as a cover. As shown in FIG. 1A, opening 12 serves as an inlet and opening 14 serves as an outlet. The openings 12, 14 were used to make connections to a micro-fluidic cavity 16 formed in PDMS layer 18. Inlet tubing 26 is shown connected to nanoport 22 and outlet tubing 28 is shown connected to nanoport 24.

Irreversible sealing between glass slide 20 and PDMS layer 18 was accomplished by first thoroughly rinsing the PDMS replica and the drilled glass plate with methanol and then drying them separately under a $N_2$ stream. The two pieces 18 and 20 were then placed in an oxygen plasma cleaner (Harrick plasma cleaner/sterilizer PDC-32G) and oxidized at medium power for 20 seconds. The PDMS (channel side) and the glass were brought into conformal contact immediately after removal from the plasma cleaner and an irreversible seal formed spontaneously. This seal was sufficiently strong that the two pieces could not be separated without destroying the assembled micro-fluidic device. Once it was sealed, two nanoports 22, 24 (Upchurch) were attached to the glass side 20 using epoxy rings and baking for 2 hours at 200° C.

Solid Support Preparation

Modification of the support material was performed as disclosed in Nakamura, et al., "Effect of Type and Concentration of Coupling Buffer on Coupling Yield in the Coupling of Proteins to a Tresyl-Activated Support for Affinity Chromatography", J. Chromatogr., 513, 367–369 (1990). Briefly, 10.0 mg of Toyopearl particles were washed 3 times with 1.0 mL of phosphate buffer (1.0 M, pH=8.00) and mixed with 1.5 mg of lysozyme (150 µl, 10 mg/ml). The mixture was left to stand with periodical agitation for 4 hours at 25° C. (ECHO Therm incubator). The particles were washed four times with 1.0 mL of phosphate buffer (1.0 M, pH=8.00, 3 M NaCl) to remove any unspecifically bound protein. In order to cap the remaining tresyl-chloride reactive groups, the particles were re-suspended in 1.0 mL of ethanolamine (1.0 M, pH=8.00), left with periodical agitation for another 4 hours at 25° C., washed four times with 1.0 mL of phosphate buffer (1.0 M, pH=8.00) and re-suspended in 1.0 mL of the same washing solution.

The cavity of the device was packed with the modified particles by flushing the cavity with a slurry of the modified particles at 5.0 µL/min. The flow rate was subsequently kept under 2.0 µL/min to insure that the bed was not disturbed.

Figure 1B:
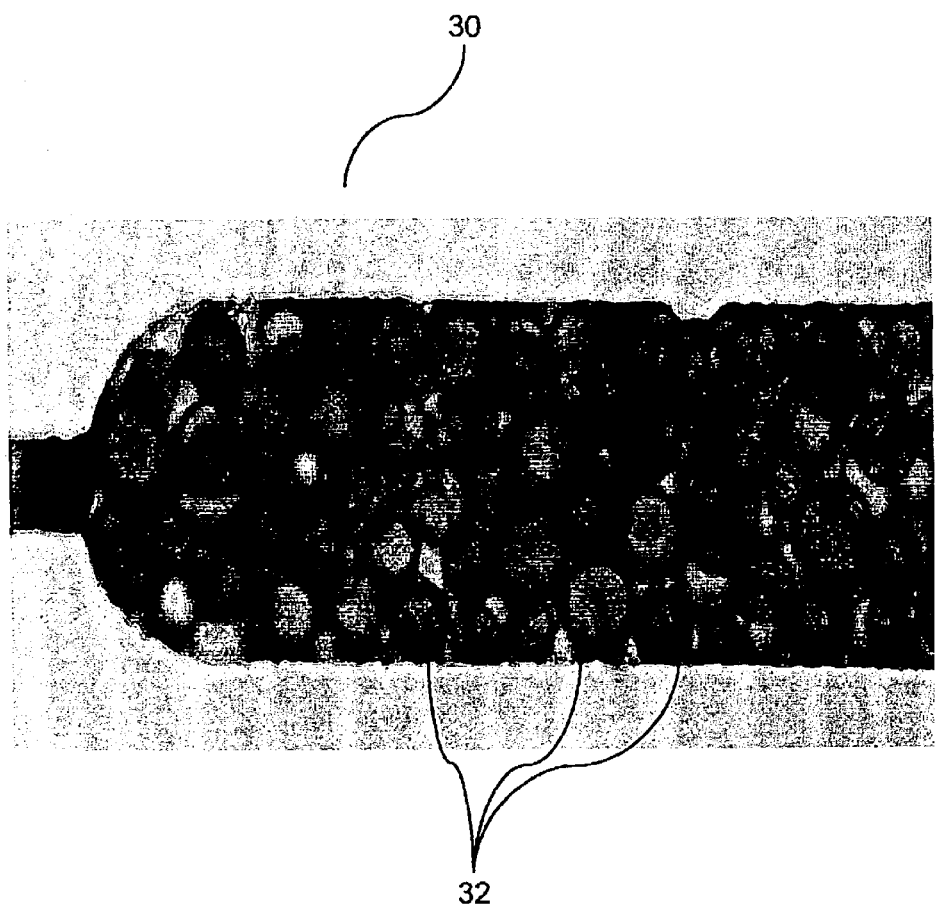
FIG. 1B is a photomicrograph of a micro-fluidic device packed with particles according to the invention.

A photomicrograph of a device having a packed cavity according to the invention is shown in FIG. 1B. As can be seen in FIG. 1B, the cavity 30 of the micro-fluidic device is filled with particles 32 comprising the solid support.

3-Results and Discussion

To calculate k', it was assumed that the $t_R$ for lysozyme obtained at pH=4.2 and 2% (w/v) NaCl corresponds to $t_m$ because at those conditions the net interactions between lysozyme molecules is almost zero (George, et al., "Predicting Protein Crystallization from a Dilute Solution Property", Acta Crystalogr., D 50, 361 (1994)). As was mentioned before, the chromatographic parameter k' (from equation 1) was used to evaluate the interaction because it allows a simple and accurate correlation between SIC and SLS data.

3-1-Effect of NaCl Concentration

Figure 2:
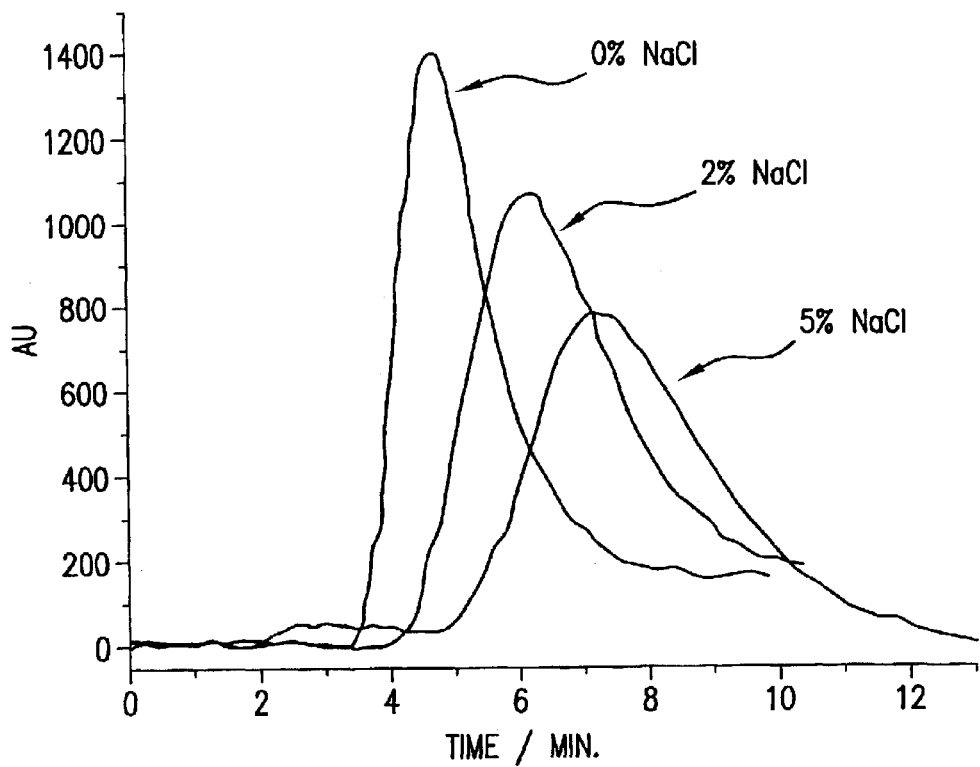
FIG. 2 is a graph showing representative chromatograms for the self-interaction of LYS at different NaCl concentrations generated using a micro-fluidic device according to the invention.
Figure 3:
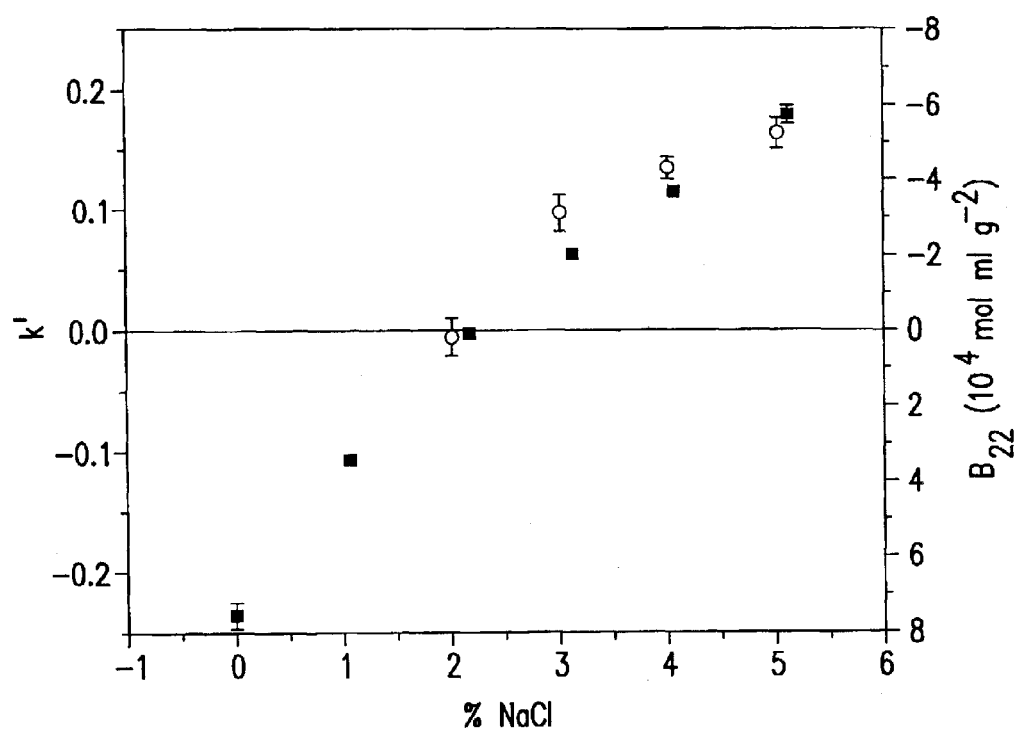
FIG. 3 is a graph showing k' (■) and $B_{22}$ (○) as a function of % NaCl wherein k' was measured using a micro-fluidic device according to the invention and $B_{22}$ values were obtained using static light scattering.

Lysozyme ($t_{RLZM}$) retention times were analyzed as a function of the NaCl concentration in the mobile phase (HAc/NaAc, pH=4.20). In FIG. 2, three chromatographic peaks for lysozyme, obtained at 0%, 2% and 5% NaCl are plotted. As can be observed, there is a clear difference in retention times for the same protein sample at all three conditions. A change in peak shape can be observed as NaCl concentration increases, due to stronger interactions of the protein molecules In FIG. 3, the k' values for lysozyme are seen to increase as a function of NaCl concentration. In order to show the correlation between SIC and SLS, the results obtained by SIC (k') and by SLS ($B_{22}$) as a function of NaCl concentration for lysozyme were also plotted in FIG. 3. Working at lower NaCl concentrations (positive $B_{22}$ values), the sample eluted faster than the $t_m$ marker (negative k') indicating the presence of net repulsive forces. On the other hand, working at higher NaCl concentrations, (negative $B_{22}$ values) the retention time was longer than the $t_m$, indicating net attractive interactions. As can be seen, there is a strong correlation between the experimental and literature data.

3-2-Effect of Flow Rate

Figure 4A:
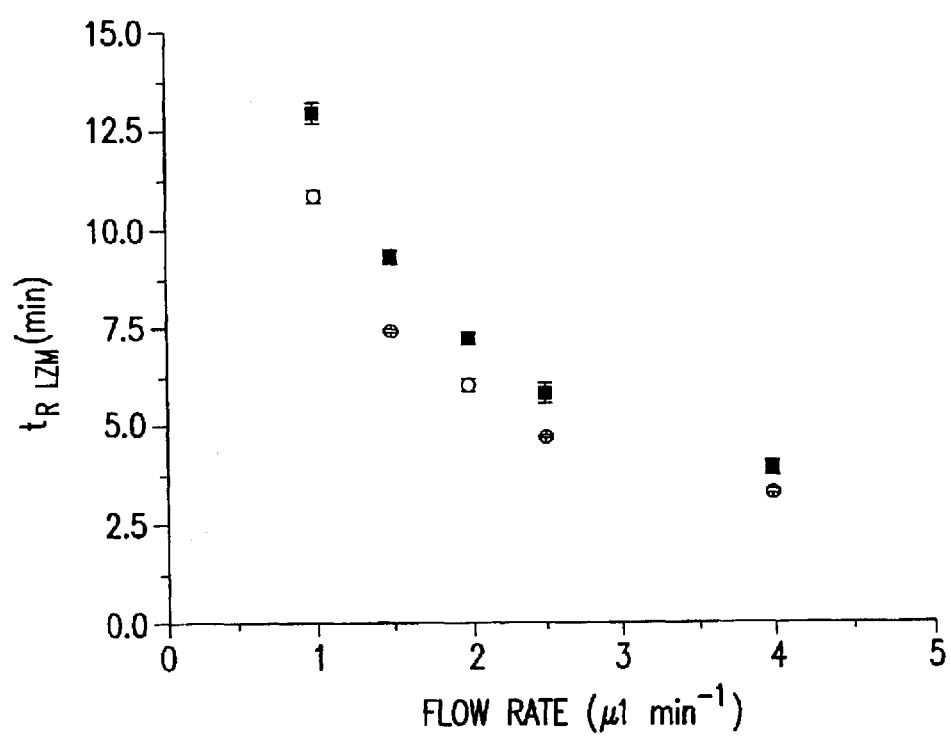
FIG. 4A is a graph showing retention time as a function of flow rate for LYS in a micro-fluidic device according to the invention.

The flow rate ($F_R$) can influence not only the time that the sample will interact with the stationary phase, but also the sampling rate. Lower flow rates result in higher $t_R$ values increasing the sensitivity of the system to changes in $B_{22}$ but also increasing the analysis time and decreasing the sampling rate. The dependence of $t_R$ as a function of flow rate for lysozyme in a HAc/NaAc 0.1 M, pH=4.2, 2% NaCl (■) and 2% NaCl (○) are shown in FIG. 4A. As can be seen in FIG. 4A, a gradual decrease in the $t_R$ occurs as the flow rate increases for both sets of data.

Taking into account the compromise between reasonable $t_R$ values and the relative error of the measurement, a flow rate of 1 μL/min was selected as optimum. Under these conditions, the protein elutes from the cavity in less than 7 minutes and both sets of data are clearly different. For higher flow rates, the relative error is too large, making it very difficult to distinguish between the $t_m$ and $t_R$. These results also show that the flow rate can be decreased to obtain higher resolution, if needed.

Figure 4B:
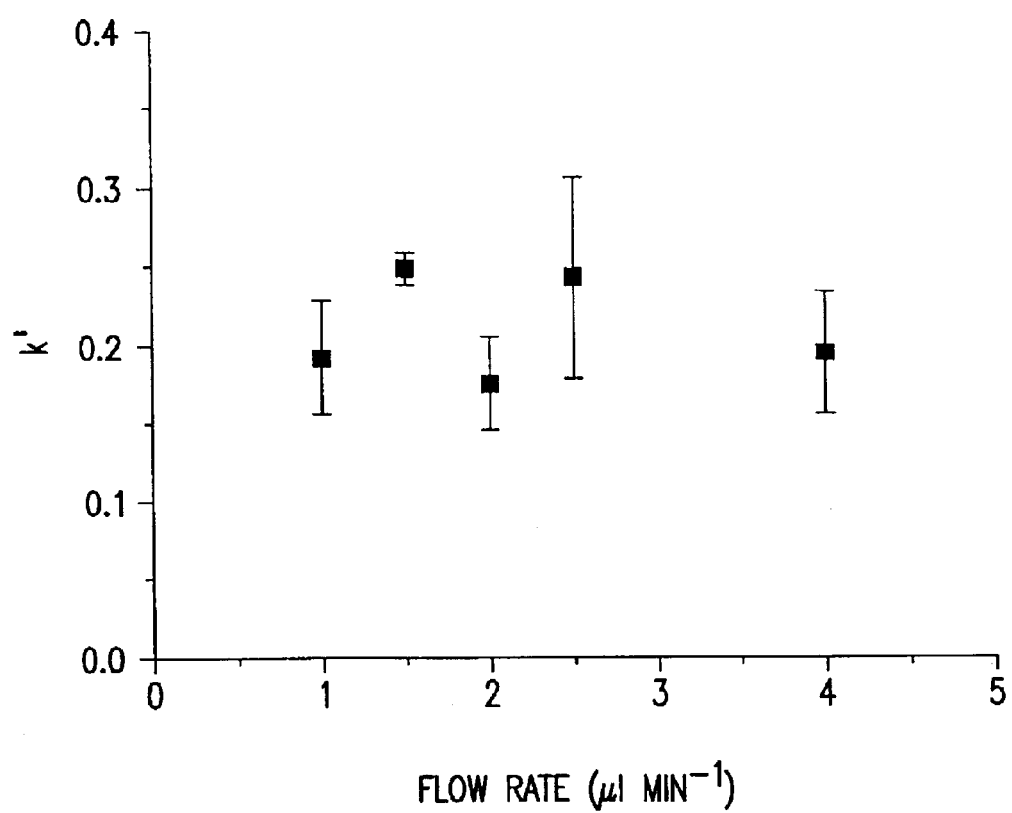
FIG. 4B is a graph showing k' as a function of flow rate wherein k' is calculated from the retention time values shown in FIG. 4A.

FIG. 4B shows k' as a function of the flow rate for lysozyme in a HAc/NaAc 0.1 M, pH=4.2, 2% NaCl (■). As can be seen from FIG. 4B, no significant change in k' is observed with flow rate thus indicating that the same adsorption mechanism is occurring at every studied flow rate.

3-3-Effect of Protein Concentration

Figure 5:
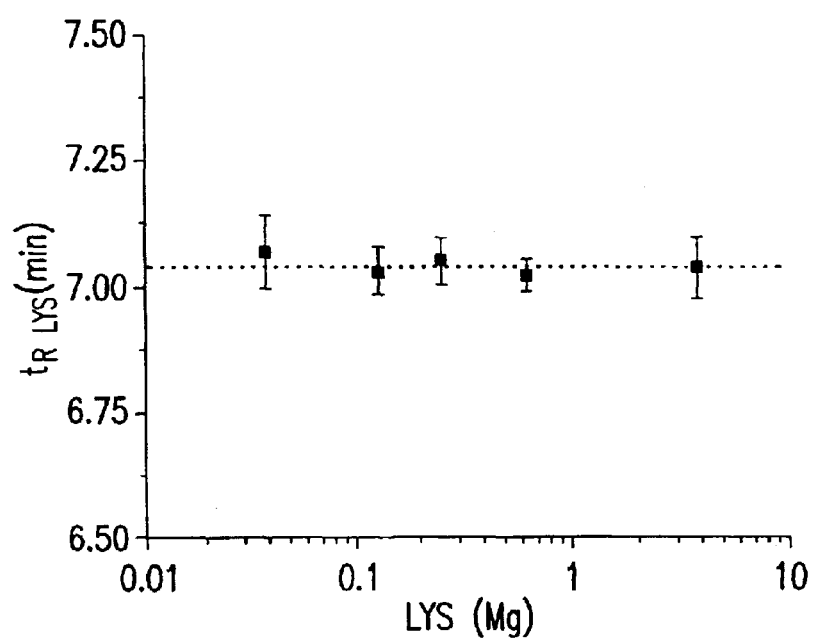
FIG. 5 is a graph showing the retention time of LYS as a function of the amount of protein injected using a micro-fluidic device according to the invention.

For most forms of chromatography, the adsorption isotherm is linear at low injection concentrations and therefore the retention is independent of the injection concentration. In order to study the effect that sample concentrations can have on the chromatogram, different samples were injected from 0.18 mg/ml to 19.4 mg/ml. As can be observed in FIG. 5, there is no appreciable change in the peak position (7.04±0.02 min) between different concentration samples. The shape of the peak was also substantially the same at all concentrations tested (not shown).

The absence of a concentration effect can be important for two reasons. First, the errors produced by weighing the protein to prepare the samples will have a minimal effect on the results. Second, a lower concentration of protein can be used thereby minimizing the protein consumption. In this case, the lowest injected amount was 37 ng. Using this amount of protein, a signal/noise ratio of 3 was obtained thus indicating that even smaller amounts of protein can be utilized.

3-4-Effect of the Amount of Bound Protein

As was previously suggested, lower buffer concentrations can result in lower coupling efficiencies and lower surface coverage. In order to evaluate the effect of the amount of protein bound on the k' value, different sets of particles were prepared using different buffer concentrations during the coupling reaction. The efficiency was evaluated by measuring the absorbance at 280 nm (Beckman DU-640 Spectrophotometer) of the protein solution before and after the incubation using 2.63 $mg^{-1}$ ml $cm^{-1}$ as the extinction coefficient. The obtained results for the coupling procedures are shown in Table 1 below:

TABLE 1

| Protein | Buffer concentration | Efficiency |
|---------|---------------------|------------|
| LYS | 0.075 M | 47% |
| LYS | 0.75 M | 70% |

Micro-fluidic devices according to the invention will preferably have an internal volume) i.e., a cavity volume) of less than 1 ml, more preferably less than 100 μl, and most preferably less than 10 μl.

Although a cavity having a channel shape is illustrated in the figures, the cavity of the micro-fluidic devices according to the invention can have any shape. Cavities having an elongate shape are preferred. The cavity of the micro-fluidic device is provided with inlet and outlet openings such that fluid entering the inlet flows through the channel and exits the cavity through the outlet. The inlet and outlet are preferably formed in the cover layer prior to securing the cover layer to the channel layer. However, the inlet and outlet can also be formed in the channel layer.

Micro-fluidic devices according to the invention are preferably made by casting a curable polymer composition onto a positive relief surface comprising a raised region, curing the polymer composition, and removing the cured polymer from the positive relief surface to form the channel layer. The channel layer will have a channel corresponding to the raised elongate region. A cover can then be disposed on the cured polymer layer over the channel to form a cavity. The cover layer can be secured to the channel using any means known in the art. According to a preferred embodiment of the invention, the channel layer is secured to the cover layer by treating the opposing surfaces of each layer with an oxygen plasma and bringing the treated surfaces into conformal contact. The cavity can then be filled or packed with a solid support having a biomolecule (e.g., a protein or ligand) immobilized on a surface thereof.

The positive relief surface used to form the channel can be made by coating a photoresist onto a substrate, disposing a mask having an elongate pattern on the photoresist, exposing the photoresist through the mask, and removing exposed or unexposed portions of the photoresist to form the positive relief surface. The elastomer composition preferably comprises poly(dimethyl siloxane), although other elastomer compositions can also be used. The photoresist can be a negative photoresist such that unexposed portions of the photoresist are removed to form the positive relief surface. Alternatively, the photoresist can be a positive photoresist such that exposed portions of the photoresist are removed to form the positive relief surface.

The polymer composition used to form the channel layer can be a silicon containing polymer composition. The polymer composition can also be an elastomer composition. Exemplary elastomer compositions include silicon containing elastomer compositions. The channel layer can also be made from a glass composition. Exemplary glass compositions include silicon containing glass compositions. Channel layers made from glass can be manufactured using known glass forming techniques. For example, molten glass can be cast onto a suitable (i.e., high temperature) positive relief surface.

The material used to form the channel layer can be chosen based on the rigidity requirements of the end use application. For example, where high rigidity is required a glass composition can be used. For low rigidity requirements, a polymer or elastomer composition can be employed.

Any type of solid support can be used according to the invention. The solid support preferably comprises a plurality of particles having a biomolecule immobilized thereon. Suitable particles include polymer particles. Exemplary particles include, but are not limited to, gel particles. The diameter of the particles and the material used as a solid support can be varied based upon the requirements of the application.

From the foregoing, it will be appreciated that, although specific embodiments of the invention have been described herein for purposes of illustration, various modifications may be made without deviating from the spirit and scope of the invention.

What is claimed is:

1. A method of measuring non-binding interactions between a first biomolecule and a second biomolecule to determine an osmotic second virial coefficient, the method comprising:

flowing a solution through a micro-fluidic device comprising a solid support contained in a cavity, wherein the first biomolecule is immobilized on a surface of the solid support;

injecting a sample comprising the second biomolecule into the flowing solution upstream of the cavity; and measuring the time (retention time, $t_R$) required for the second biomolecule to emerge from the cavity;

wherein the cavity has an internal volume of 100 µl or less, and wherein the retention time ($t_R$) is a measure of a degree of non-binding interactions between the first biomolecule and the second biomolecule which correlates with the osmotic second virial coefficient for the first biomolecule and second biomolecule pair.

2. The method of claim 1, further comprising:

determining the time required ($t_m$) for a non-interacting marker molecule to pass through the cavity, said marker molecule having a substantial absence of interactions with the first biomolecule; and calculating a chromatographic capacity factor (k') from $t_R$ and $t_m$, wherein $$k' = \frac{t_R - t_m}{t_m}.$$

3. The method of claim 1, wherein the first and second biomolecules are the same biomolecule.

4. The method of claim 1, wherein the first and second biomolecules are different biomolecules.

5. The method of claim 2, further comprising:

correlating k' with the osmotic second virial coefficient describing the non-binding interactions between the first and the second biomolecule.

6. The method of claim 1, wherein the first and second biomolecules are both lysozyme.

7. The method of claim 1, wherein the first and second biomolecules are proteins.

8. The method of claim 1, wherein the first biomolecule is a ligand and the second biomolecule is a protein.

9. The method of claim 1, wherein the first biomolecule is a drug and the second biomolecule is a protein.

10. The method of claim 1, wherein the sample further comprises a compound, and wherein the time required for the second biomolecule to emerge from the cavity ($t_R$) is a measure of the degree of non-binding interactions described by the osmotic second viral coefficient between the first biomolecule and the second biomolecule in the presence of the compound.

11. The method of claim 1, wherein the cavity has an internal volume of 10 µl or less.

* * * * *